United States Patent
Kusakari et al.

(10) Patent No.: US 7,369,759 B2
(45) Date of Patent: May 6, 2008

(54) EYE IMAGE PICKUP APPARATUS, IRIS AUTHENTICATION APPARATUS AND PORTABLE TERMINAL DEVICE HAVING IRIS AUTHENTICATION FUNCTION

(75) Inventors: Takashi Kusakari, Yokohama (JP); Jyoji Wada, Yokohama (JP); Tamotsu Kaneko, Zama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 860 days.

(21) Appl. No.: 10/400,835

(22) Filed: Mar. 27, 2003

(65) Prior Publication Data
US 2006/0120707 A1 Jun. 8, 2006

(51) Int. Cl.
*G03B 29/00* (2006.01)
*A61B 3/15* (2006.01)

(52) U.S. Cl. ............... 396/18; 348/78; 348/333.03

(58) Field of Classification Search ............... 396/14, 396/18, 376; 382/117; 348/78, 333.02, 348/333.03
See application file for complete search history.

(56) References Cited

U.S. PATENT DOCUMENTS

| 6,333,988 | B1 * | 12/2001 | Seal et al. .................. 382/117 |
| 2001/0026632 | A1 * | 10/2001 | Tamai ........................ 382/116 |
| 2002/0008768 | A1 * | 1/2002 | Takada et al. ......... 348/333.03 |
| 2002/0025145 | A1 * | 2/2002 | Nanjyo ........................ 396/18 |
| 2003/0169334 | A1 * | 9/2003 | Braithwaite et al. .......... 348/78 |

FOREIGN PATENT DOCUMENTS

| JP | 5-84166 | 12/1993 |
| JP | 10-40386 | 2/1998 |

* cited by examiner

*Primary Examiner*—W. B. Perkey
*Assistant Examiner*—Rishi S. Suthar
(74) *Attorney, Agent, or Firm*—Pearne & Gordon LLP (57) ABSTRACT

An iris authentication apparatus includes a camera for obtaining the image of an eye; a display panel arranged on the same plane as where the lens of the camera is arranged; and guide character generation means, wherein a guide character is displayed on a display panel, and the eye of a person to be authenticated who watches the guide character is guided. As a result, a satisfactory iris image can be obtained by the iris authentication apparatus of one camera type that does not have a zooming function, so that the iris authentication apparatus that can be mounted to a small body, such as a portable telephone, can be provided.

30 Claims, 5 Drawing Sheets

EYE IMAGE PICKUP APPARATUS, IRIS AUTHENTICATION APPARATUS AND PORTABLE TERMINAL DEVICE HAVING IRIS AUTHENTICATION FUNCTION

BACKGROUND OF THE INVENTION

1. Field of the Invention

The present invention relates to an eye image pickup apparatus used by an iris authentication system for identifying an individual using iris information of a human being or another animal.

2. Description of the Related Art

The technique disclosed in Japanese Examined Patent Publication No. H05-084166(B2) is well known as an example technique for obtaining the iris image of a human being by a camera and authenticating an individual. Generally, to perform individual authentication, the iris authentication apparatus emits near-infrared light to the eye of a person to be authenticated, photographs the eye image using a single video camera having a telephoto lens, extracts iris information from the obtained eye image, compares the iris information with data already registered to an iris information database.

For the personal authentication, the accuracy for photographing the eye image is the great factor in order to exactly extract the iris information of a person to be authenticated, and his or her eye of a predetermined size must be photographed within a screen. Therefore, the position of the eye is detected from the image of the entire face, and only the eye is zoomed up by a zoom lens to obtain the eye image of a predetermined size.

An iris authentication apparatus of two-camera type, disclosed in Japanese Unexamined Patent Publication No. H10-040386, includes a wide-angle camera for photographing the entire face and a moving telephoto camera for photographing only the eye portion. According to this apparatus, the position of the eye is detected in the image of the face or the upper body obtained by the wide-angle camera, and is transmitted as coordinate data in the wide-angle image to the movement controller of the moving telephoto camera. Based on the positional information, the eye image of a predetermined size is photographed by aiming the moving telephoto camera at the eye of a target person, and detailed iris information is thus obtained.

However, when the iris authentication apparatus is mounted on a terminal device, such as a portable telephone, for which the reduction of the size, the weight and the price is strongly demanded, the following problems have occurred. For an iris authentication apparatus that employs a single camera to zoom up and photograph an iris image, a high-level zooming function must be provided so as to photograph a wide-angle face image and an telephoto eye image, so that the reduction of the size and the price of a lens can not be implemented.

Further, since the iris authentication apparatus of two-camera type must be equipped with two cameras, a wide-angle camera and a telephoto camera having a moving function, the size and the weight of the camera portion can not be reduced. Further, since a driving mechanism and circuit for moving the telephoto camera are also required, it is practically impossible that this iris authentication apparatus is mounted on the portable terminal device.

SUMMARY OF THE INVENTION

To resolve these problems, it is one objective of this invention to provide an eye image pickup apparatus that can obtain a satisfactory iris image without requiring a zooming function and a driving mechanism, an iris authentication apparatus, and a portable terminal device having an iris authentication function.

To achieve this objective, an eye image pickup apparatus according to the invention includes a pickup camera for photographing an image of an eye; display means located on the same plane as the position where the lens of the pickup camera is arranged; and guide character generation means for displaying a guide character on the display means to guide the eye that aims at the guide character.

With this configuration, when a person to be authenticated looks at the guide character displayed on the display means, his or her eye is guided to the optimal location and at the optical distance, so that even an apparatus that employs a single camera and does not include a zooming function can obtain an enlarged iris image appropriate for the iris authentication process. Furthermore, since the person to be authenticated is permitted to "look at" the guide character, successfully the person's eye is widely opened.

It is preferable that the guide character be displayed with being superimposed with the image of the eye obtained by the pickup camera. With this configuration, the person to be authenticated can easily and intuitively identify where his or her eye should aim, and can move his or her eye with the guide character as a target.

The guide character is across-shaped character where an intersection is located at the center of a photographed image, or a frame-shaped character that corresponds to the external circumference of an iris of a predetermined size, or a directional character indicating the direction in which the eye should move, or multiple concentric characters at the center of a photographed image. With this configuration, the person to be authenticated can easily and intuitively identify at which camera his or her eye should aim.

It is preferable that, when an iris in an eye image is smaller than a predetermined size, the multiple concentric characters be turned on or blink in order from the innermost circle to the outermost circle, and that, when the iris is greater than the predetermined size, the multiple concentric characters be turned on or blink in order from the outermost circle to the innermost circle. With this configuration, the person to be authenticated can easily and intuitively identify whether he or she is positioned too close to or too far from the camera.

The guide character generation means generates multiple types of guide characters independently or at the same time. With this configuration, the guide characters can be generated appropriate for guiding the eye of the person to be authenticated to the optical location.

The guide character generation means generates a guide character indicating that an image of a predetermined size has been photographed for a focused iris in an eye image, and when the image of the predetermined size is obtained for the focused iris in the eye image, the guide character is displayed on the display means. With this configuration, the person to be authenticated is notified of the image satisfactory for the iris authentication process.

When the image of the predetermined size is photographed for the focused iris in the eye image, the guide character generation means changes the color of a background displayed on the display means. Or, when the image of the predetermined size is photographed for the focused iris in the eye image, the guide character generation means continuously displays the eye image as a static image on the display means. Also with this configuration, the person to be authenticated can be notified that the image appropriate the iris authentication process is obtained.

The eye image pickup apparatus further includes: voice notification means for, when the image of the predetermined size is photographed for the focused iris in the eye image, issuing a voice notification that the image of the predetermined size is obtained for the focused iris in the eye image. Also with this configuration, the person to be authenticated is notified that the image appropriate for the iris authentication process has been obtained.

To achieve the objective, an iris authentication apparatus includes: the thus arranged eye image pickup apparatus; and iris authentication means for determining through comparison whether an image of a predetermined size for a focused iris in an eye image, which is obtained by the eye image pickup apparatus, matches a registered iris image.

Since the iris authentication apparatus comprises the eye image pickup apparatus and the iris authentication means, an iris authentication apparatus of one camera type having no zooming function can be employed. Thus, the iris authentication apparatus of a low cost can be provided.

In addition, to achieve the objective, a portable terminal device having an iris authentication function can be provided by mounting the iris authentication apparatus of this invention. Further, when the portable terminal device is a portable telephone, the display unit of the portable telephone is employed also as the display means.

Since the iris authentication apparatus is one camera type having no zooming function, the size and the weight thereof can be reduced, and this apparatus can be easily mounted on a small portable terminal, such as a portable telephone. Further, since an iris image appropriate for the iris authentication process can be obtained, high security is ensured, and the function serving as electronic money or a credit card can be mounted in the portable terminal device.

DETAILED DESCRIPTION OF THE PREFERRED EMBODIMENT

An embodiment of the present invention will now be described while referring to the drawings.

Figure 1:
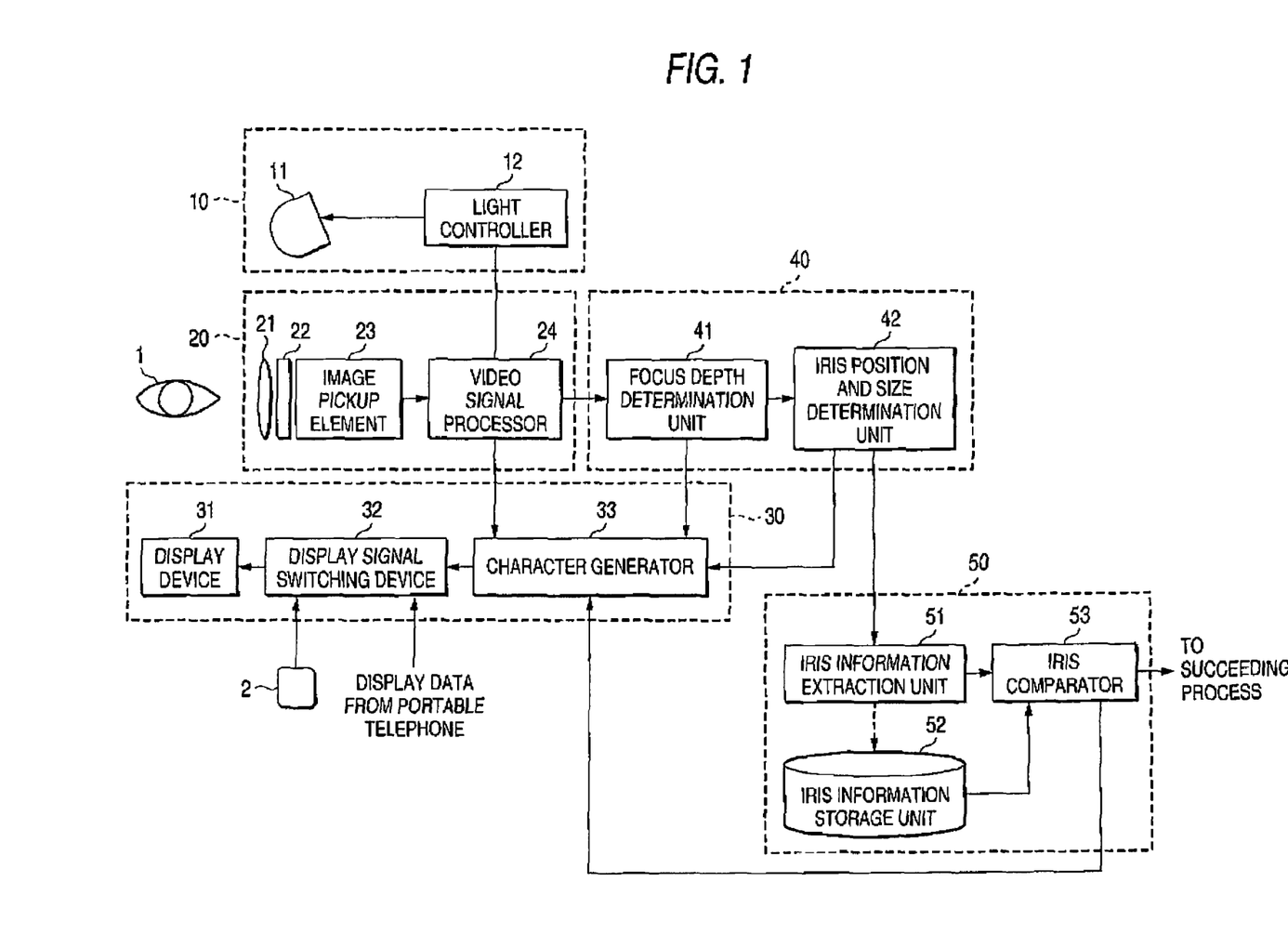
FIG. 1 is a diagram showing the configuration of an iris authentication apparatus according to one embodiment of the present invention.

FIG. 1 is a diagram showing the configuration of an iris authentication apparatus according to the embodiment of the present invention. This iris authentication apparatus includes: a lighting unit 10, an imaging unit 20, a display unit 30, a preprocessor 40 and an authentication unit 50.

The lighting unit 10 includes a near-infrared light 11 and a light controller 12, and emits, toward the eye of a person to be authenticated, the amount of light appropriate for acquisition of an eye image.

The imaging unit 20 includes a lens 21, a visible light cut filter 22, an image pickup element 23 and a video signal processor 24. An eye 1 of a person to be authenticated is irradiated by the near-infrared light 11 of the lighting unit 10, and the light reflected from the eye 1 is passed through the lens 21 and the visible light cut filter 22 to the image pickup element 23.

The reflected light is received by the image pickup element 23 and is photoelectrically converted into an electrical signal, and this electrical signal is transmitted to the video signal processor 24. The video signal processor 24 extracts a video signal element from the received electrical signal, performs a process necessary for a video signal, such as gain adjustment, and outputs the image data for the eye 1 of the person to be authenticated.

The preprocessor 40 includes a focus depth determination unit 41 and an iris position and size determination unit 42. The focus depth determination unit 41 performs edge detection by using the image data of the eye 1 obtained by the imaging unit 20, and determines the depth of focus. When a desired depth of focus is not obtained, the focus depth determination unit 41 transmits the results to the display unit 30.

The iris position and size determination unit 42 performs the pattern matching for the image data of the eye 1 obtained by the imaging unit 20, and determines the position and the size of the iris. When desired position and size of the iris are not obtained, the iris position and size determination unit 42 transmits the results to the display unit 30.

When, by repeating this process, the position and the size of the iris and the depth of focus, which are image data of the eye 1, have reached desired values, the image data of the eye 1 are output to the authentication unit 50 at the succeeding stage.

The authentication unit 50 includes an iris information extraction unit 51, an iris information storage unit 52 and an iris comparator 53. When the iris authentication apparatus is in the registration mode, the iris information extracted by the iris information extraction unit 51 is stored in the iris information storage unit 52. When the iris authentication apparatus is in the authentication mode, the iris comparator 53 compares the iris information obtained by the iris information extraction unit 51 with the data stored in the past in the iris information storage unit 52 to determine whether the person to be authenticated is a person registered in the past. The authentication results are transmitted to the succeeding processing units, and also to the display unit 30 to notify the person to be authenticated of the authentication results.

The display unit 30 includes a display device 31, such as a liquid crystal display monitor, a display signal switching device 32 and a character generator 33. As is shown in FIG. 2, as guide characters to be displayed on the display device 31, the character generator 33 generates a cross-shaped guide character 66, a desired iris frame guide character 67, a direction instruction guide character 68 and a concentric guide character 69 of multiple circles, independently, or as a combination of them.

Figure 2:
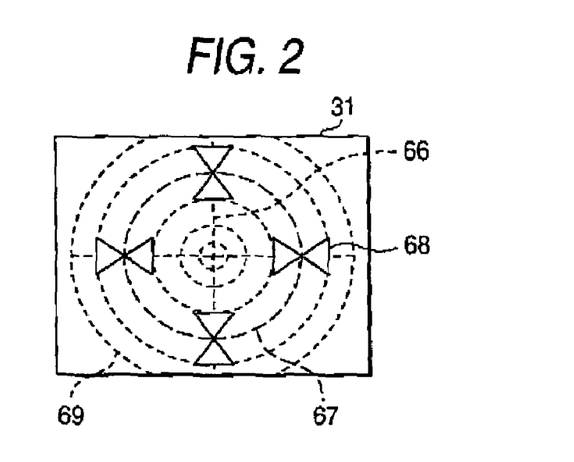
FIG. 2 is a diagram for explaining guide characters used by the iris authentication apparatus according to the embodiment of the invention.

The character generator 33 employs the information received from the preprocessor 40 and the authentication unit 50 to select a guide character from those shown in FIG. 2, superimposes the selected guide character with the video signal received from the imaging unit 20, and outputs the results to the display signal switching device 32.

In accordance with switching information entered at an external button 2 of the portable terminal, the display signal switching device 32 switches between the display data received from the portable terminal device and the display signal received from the character generator 33, and outputs the signal or data to the display device.

Figure 3:
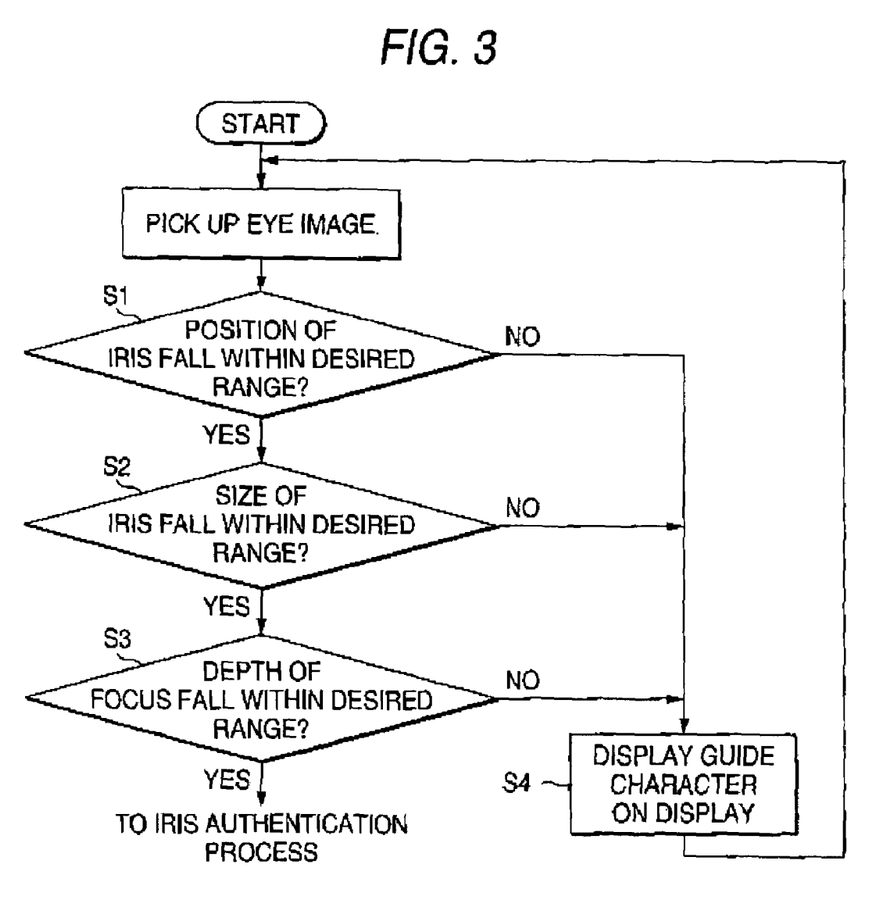
FIG. 3 is a flowchart showing the iris image acquisition processing performed by the iris authentication apparatus according to the embodiment of the invention.

FIG. 3 is a flowchart showing the processing performed by the preprocessor 40 of the iris authentication apparatus in FIG. 1. When the image of the eye of a person to be authenticated is transmitted from the imaging unit 20 in FIG. 1, first at step S1, a check is performed to determine whether the iris in the eye image is located within a predetermined range. When the iris is not located in the predetermined range, program control proceeds to step S4, whereat the character generator 33 generates the pertinent guide character. Program control thereafter waits until the eye image is input at the next time.

When the iris in the eye image is located within the predetermined range, program control advances from step S1 to step S2, whereat a check is performed to determine whether the size of the iris falls within a predetermined range. When the size of the iris does not fall within the predetermined range, program control proceeds to step S4, whereat the character generator 33 generates the pertinent guide character.

When the size of the iris falls within the predetermined range, program control advances from step S2 to step S3, whereat a check is performed to determine whether the depth of focus for the eye image falls within a predetermined range. When the depth of focus does not fall within the predetermined range, program control proceeds to step S4, and the character generator 33 generates the pertinent guide character. That is, since the authentication is disabled when the obtained eye image is not clear, guide characters such as "please get still" is displayed on the display device 31.

When the processes at steps S1 to S3 have been completed, the processor 40 transmits the eye image received from the imaging unit 20 to the authentication unit 50 at the succeeding stage for performing the iris authentication process.

Figure 4:
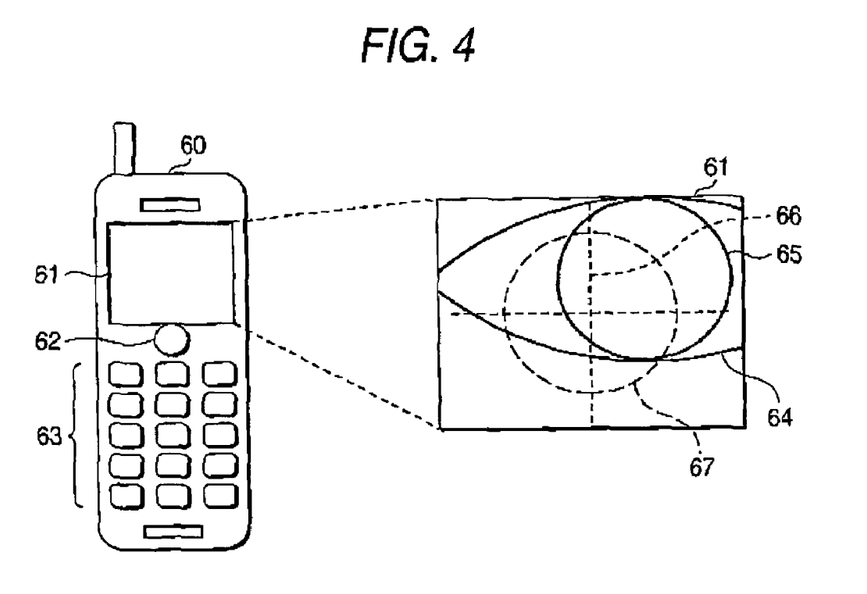
FIG. 4 is a diagram showing the external appearance of a portable telephone having an iris authentication function according to the embodiment of the invention.

The display form for the guide character will now be specifically described. When the iris authentication apparatus in FIG. 1 is mounted to a portable telephone, the guide character is displayed on the liquid crystal display panel of the portable telephone. The outer appearance of a portable telephone 60 having an iris authentication function is shown on the left side in FIG. 4. As is shown in FIG. 4, a liquid crystal display panel 61 and a camera 62 are located closely on the same plane. A person to be authenticated, i.e., the owner of the portable telephone 60, employs the external button 63 to set the portable telephone 60 to the iris authentication mode. When the portable telephone 60 is set to the iris authentication mode, the portable telephone 60 sets the screen of the liquid crystal panel 61 to the display for iris authentication.

The enlarged appearance of the liquid crystal display panel 61 is shown on the right side in FIG. 4 when the portable telephone 60 is in the iris authentication mode. In this enlarged diagram, a cross-shaped guide character 66 for guiding the center position of the iris and a desired iris frame guide character 67 for guiding the iris of a target size are displayed in addition to an eye image 64 of a person to be authenticated.

While watching the liquid crystal display panel 61, the person to be authenticated adjusts the position of his or her eye to the camera 62 by moving the portable telephone 60. At this time, since the liquid crystal display panel 61 and the camera 62 are located very closely to each other, the line of sight, i.e., the center of the eye can be entered easily to the angle of view of the camera. In accordance with his or her eye image 64 and the indicator displayed on the liquid crystal display panel 61, the person to be authenticated can easily understand the current position of his or her eye, the point whereat the center of the eye should aim, and the size of the iris to be photographed.

Figure 5:
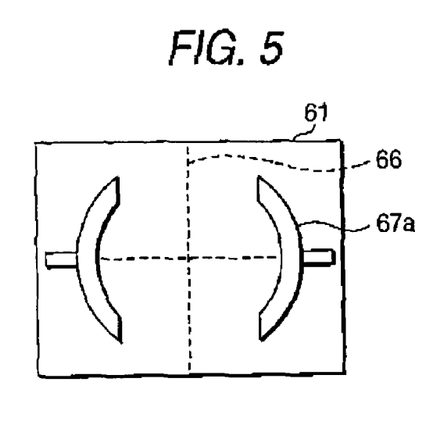
FIG. 5 is a diagram showing a modification of the guide character used by the portable telephone having the iris authentication function according to the embodiment of the invention.

In this embodiment, the iris frame guide character 67 for covering the entire circumference of the iris is employed as the guide indicator. However, the overall circumference need not be covered, and an iris frame guide character 67a in FIG. 5 employing semicircular iris frames may also be applicable.

Figure 6:
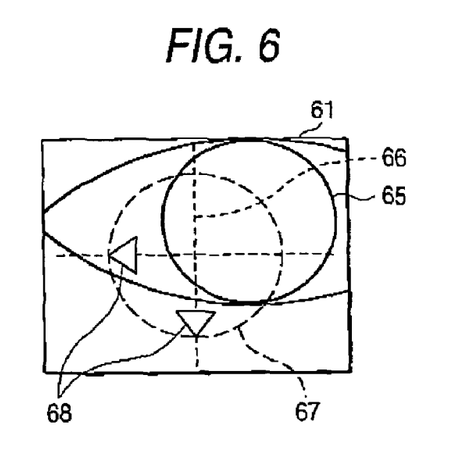
FIG. 6 is a diagram for explaining a guide indicator when the iris of a person to be authenticated is shifted right upward from a desired position of an iris.

FIG. 6 is a diagram showing an example where a direction instruction guide character 68 indicating the direction in which the iris should be moved is displayed as a guide character. In the example in FIG. 6, an image 65 of the iris of the person to be authenticated is shifted right upward from a desired position of the iris. Thus, as is shown in FIG. 6, for the position guide, the direction instruction guide character 68 is turned on or is blinking so as to move the iris left downward on the screen. In this example, two characters 68, an arrow character indicating the left direction and an arrow character indicating downward the direction, are displayed at the same time to instruct the left downward direction.

Figure 7:
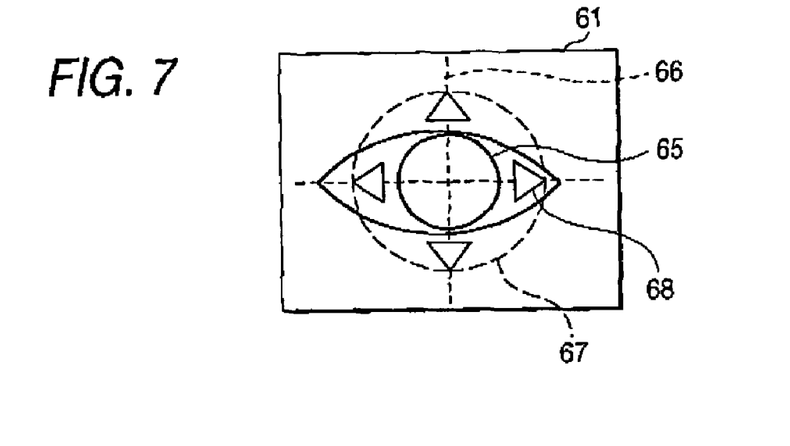
FIG. 7 is a diagram for explaining a guide indicator when the iris of a person to be authenticated is smaller than a desired size.

FIG. 7 is a diagram showing an example where a guide character is displayed to instruct the correction when the iris is smaller than a predetermined size. When the four arrows of the direction instruction guide character 68 are displayed directing outward from the center of the image, the iris is guided in the direction in which the size of the iris is enlarged (the direction in which the eye approaches the camera 62, i.e., the portable telephone 60).

Figure 8:
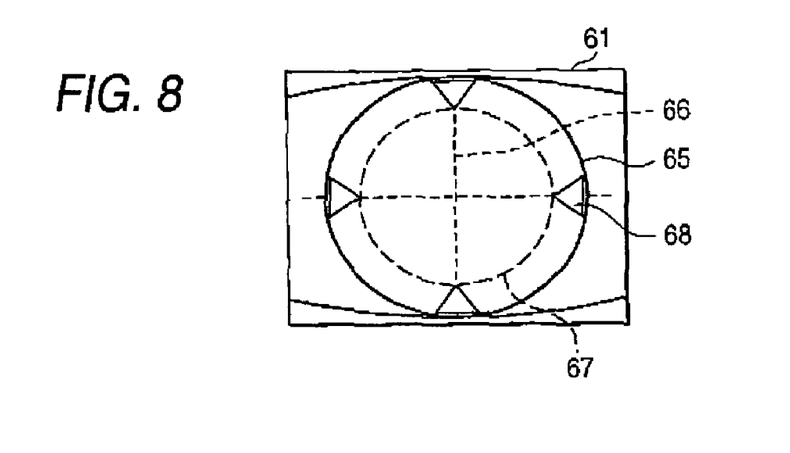
FIG. 8 is diagram for explaining a guide indicator when the iris of a person to be authenticated is larger than the desired size.

FIG. 8 is a diagram showing an example where a guide character is displayed to instruct the correction when the iris is large than the predetermined size. In this case, the four arrows of the direction instruction guide character 68 are displayed directing toward the center of the image, and the iris is guided in the direction in which the size of the iris is reduced (the direction in which the iris is farther than the camera 62, i.e., the portable telephone 60).

Figure 9:
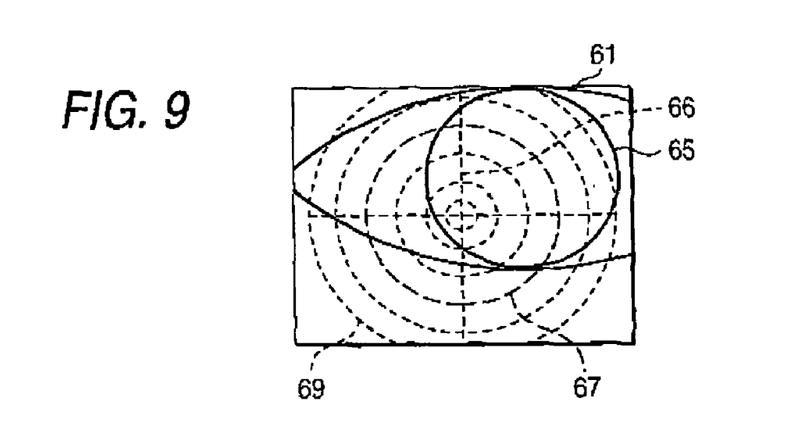
FIG. 9 is a diagram for explaining an example where the iris is guided to the center position by using a guide character.

FIG. 9 is a diagram showing an example of displaying a concentric guide character 69 employing, as a center point, the center of the screen of the display device. As is shown in FIG. 9, when the concentric guide character 69 formed of multiple concentric circles is displayed, the center of the screen (the center of the lens of the camera 62) can be clearly presented to a person to be authenticated, and the iris of the person to be authenticated can be easily guided to the center of the screen.

Figure 10:
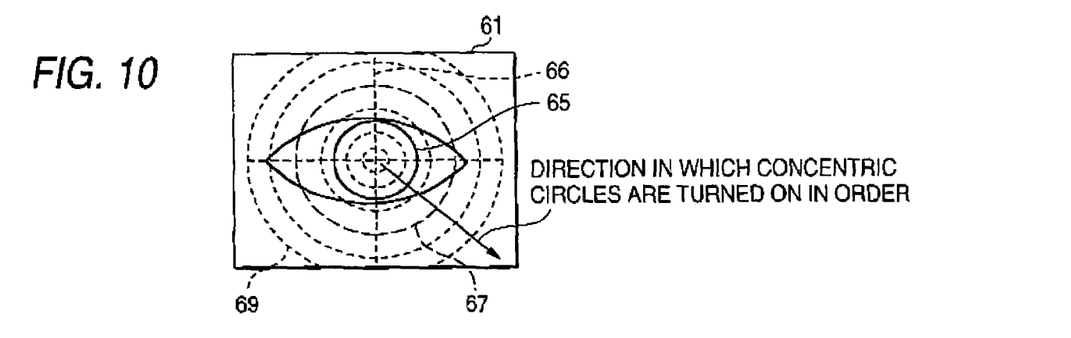
FIG. 10 is a diagram for explaining an example where the iris of a person to be authenticated is smaller than a desired size.

FIG. 10 is a diagram showing an example where the concentric guide character 69 is displayed to instruct the correction when the iris is smaller than a predetermined size. In this case, the iris must be guided in the direction in which the size of the iris is increased. Therefore, multiple concentric circles of the concentric guide character 69 are turned on or are blinking in order from the innermost circle to the outermost circle. As a result, the person to be authenticated can intuitively understand that the iris must be photographed larger, and approaches his or her eye to the camera 62 (or to the portable telephone 60).

Figure 11:
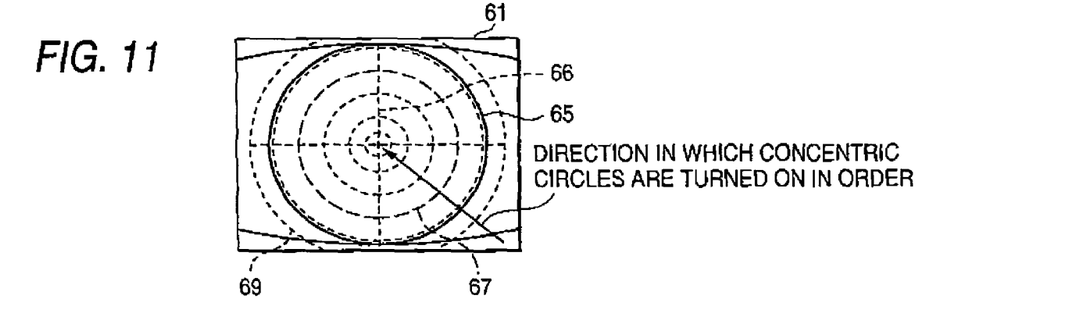
FIG. 11 is a diagram for explaining an example where the iris of a person to be authenticated is larger than the desired size.

FIG. 11 is a diagram showing an example where the concentric guide character 69 is displayed to instruct the correction when the iris is larger than a predetermined size. In this case, the iris must be guided in the direction in which the size of the iris is reduced. Therefore, multiple concentric circles of the concentric guide character 69 are turned on or are blinking in order from the outermost circle to the innermost circle. As a result, the person to be authenticated can intuitively understand that the iris must be photographed smaller, and moves his or her eye away from the camera 62 (or from the portable telephone 60).

Figure 12:
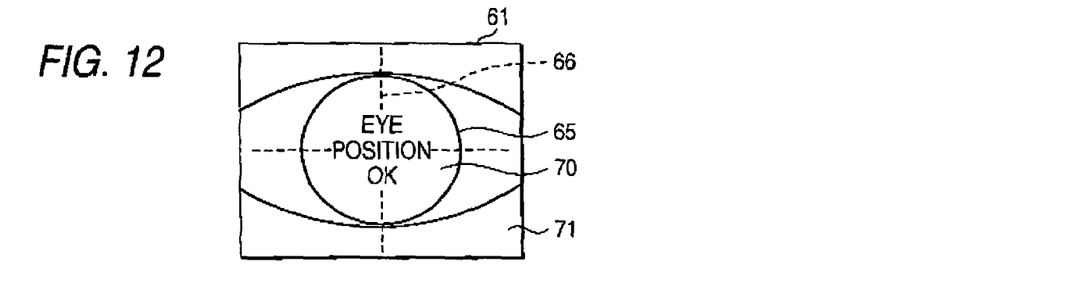
FIG. 12 is a diagram for explaining the display of a notification when the position and the size of the eye and the depth of focus fall within a predetermined range.

FIG. 12 is a diagram showing an example where, when the position and the size of the iris of the person to be authenticated and the depth of focus fall within a desired range, and the results are displayed on the display unit. In the example in FIG. 12, a results notification character 70, "eye position OK", is displayed to notify the person to be authenticated of the end of the guiding process. In addition, in the example in FIG. 12, the color of a background 71 of the liquid crystal display panel (the color of the backlight of the liquid crystal panel) is changed, so that the person to be authenticated can be more easily notified of the end of the guide process. The voice notification may also be issued, and the iris comparison results can also be provided by using the same notification means.

The various guide character types have been explained; however, these guide characters may be displayed independently, or a combination of them may be displayed. Further, a fixed value may be employed for a desired size of the iris frame guide character 67. When there are few objects to be authenticated and the iris s of the individuals are to be precisely identified, the iris frames of persons who first registered their iris data may be detected, and the registered iris frame may be employed at the next authentication time.

In this embodiment, the iris authentication apparatus has been mounted in the portable telephone. However, the present invention is not limited to the portable telephone, and can be applied when the iris authentication function is expanded to another apparatus, such as an interphone apparatus, having a display device.

According to the present invention, an eye image pickup apparatus can be provided that can obtain a satisfactory iris image without requiring a zooming function or a driving mechanism.

What is claimed is:

1. An eye image pickup apparatus comprising:
    a camera having a lens for obtaining an eye image;
    a display unit located on a same plane as the position where the lens of the camera is arranged; and
    a guide character generator for generating a guide character and allow the guide character to be displayed on the display unit to guide a position of the user's eye,
    wherein the guide character is displayed by being superimposed on the eye image obtained by the camera,
    wherein the guide character includes four arrow characters which are respectively disposed in an upward direction, a downward direction, a left direction and a right direction from a center of an image displayed on the display unit, and
    wherein the four arrow characters indicate on the image displayed on the display unit directions in which the user's eye should be moved, said directions including a forward direction, a backward direction and eight radially symmetrical directions that are perpendicular to the forward direction and the backward direction, wherein the eight radially symmetrical directions are the upward direction, the downward direction, the left direction, the right direction, a left upward direction, a right upward direction, a left downward direction and a right downward direction.

2. The eye image pickup apparatus according to claim 1, wherein the guide character includes a cross-shaped character where an intersection is located at the center of an image displayed on the display unit.

3. The eye image pickup apparatus according to claim 1, wherein the guide character includes a cross-shaped character where an intersection is located at the center of an image displayed on the display unit and a frame-shaped character corresponding to the external circumference of an iris of a predetermined size, and both of the guide characters are displayed at the same time.

4. The eye image pickup apparatus according to claim 1, wherein the guide character includes multiple concentric characters at the center of an image displayed on the display unit.

5. An eye image pickup apparatus comprising:
    a camera having a lens for obtaining an eye image;
    a display unit located on a same plane as the position where the lens of the camera is arranged; and
    a guide character generator for generating a guide character and allow the guide character to be displayed on the display unit to guide a position of the user's eye,
    wherein the guide character is displayed by being superimposed on the eye image obtained by the camera,
    wherein the guide character includes multiple concentric characters at the center of an image displayed on the display unit,
    wherein the multiple concentric characters are turned on or blink in order from an innermost circle to an outermost circle if an iris in an eye image is smaller than a predetermined size, and
    wherein the multiple concentric characters are turned on or blink in order from the outermost circle to the innermost circle if the iris is greater than the predetermined size.

6. The eye image pickup apparatus according to claim 1, wherein the guide character includes: a cross-shaped character where an intersection is located at the center of an image displayed on the display unit; a frame-shaped character corresponding to the external circumference of an iris of a predetermined size; and multiple concentric characters at the center of an image displayed on the display unit,
    wherein the guide character generator generates at least two of the characters at the same time.

7. The eye image pickup apparatus according to claim 1, wherein the guide character generator generates a guide character indicating that a size of an iris image in the eye image has been obtained within a predetermined range.

8. The eye image pickup apparatus according to claim 1, wherein the guide character generator generates a guide character indicating that a depth of focus of the eye image has been obtained within a predetermined range.

9. The eye image pickup apparatus according to claim 1, wherein the guide character generator allows to change a color of a background displayed on the display unit, if a size of an iris image in the eye image has been obtained within a first predetermined range and/or a depth of a depth of focus of the eye image has been obtained within a second predetermined range.

10. The eye image pickup apparatus according to claim 1, wherein the guide character generator continuously displays the eye image as a static image on the display unit if a size of an iris image in the eye image has been obtained within a first predetermined range and/or a depth of a depth of focus of the eye image has been obtained within a second predetermined range.

11. The eye image pickup apparatus according to claim 1, further comprising a voice notification unit for issuing a voice notification if a size of an iris image in the eye image has been obtained within a first predetermined range and/or a depth of a depth of focus of the eye image has been obtained within a second predetermined range.

12. An iris authentication apparatus comprising:
an eye image pickup apparatus including a camera having a lens for obtaining an eye image, a display unit located on a same plane as the position where the lens of the camera is arranged, a guide character generator for generating a guide character and allow the guide character to be displayed on the display unit to guide a position of the user's eye, wherein the guide character is displayed by being superimposed on the eye image obtained by the camera; and
an iris authentication unit for determining whether the image obtained in the eye image pickup apparatus matches a registered iris image,
wherein the guide character includes four arrow characters which are respectively disposed in an upward direction, a downward direction, a left direction and a right direction from a center of an image displayed on the display unit, and
wherein the four arrow characters indicate on the image displayed on the display unit directions in which the user's eye should be moved, said directions including a forward direction, a backward direction and eight radially symmetrical directions that are perpendicular to the forward direction and the backward direction, wherein the eight radially symmetrical directions are the upward direction, the downward direction, the left direction, the right direction, a left upward direction, a right upward direction, a left downward direction and a right downward direction.

13. A portable terminal comprising an iris authentication apparatus, wherein the iris authentication apparatus comprises:
an eye image pickup apparatus including a camera having a lens for obtaining an eye image, a display unit located on a same plane as the position where the lens of the camera is arranged, a guide character generator for generating a guide character and allow the guide character to be displayed on the display unit to guide a position of the user's eye, wherein the guide character is displayed by being superimposed on the eye image obtained by the camera; and
an iris authentication unit for determining whether the image obtained in the eye image pickup apparatus matches a registered iris image,
wherein the guide character includes four arrow characters which are respectively disposed in an upward direction, a downward direction, a left direction and a right direction from a center of an image displayed on the display unit, and
wherein the four arrow characters indicate on the image displayed on the display unit directions in which the user's eye should be moved, said directions including a forward direction, a backward direction and eight radially symmetrical directions that are perpendicular to the forward direction and the backward direction, wherein the eight radially symmetrical directions are the upward direction, the downward direction, the left direction, the right direction, a left upward direction, a right upward direction, a left downward direction and a right downward direction.

14. A portable telephone comprising:
a display; and
an iris authentication apparatus comprises: an eye image pickup apparatus including a camera having a lens for obtaining an eye image, a display unit located on a same plane as the position where the lens of the camera is arranged, a guide character generator for generating a guide character and allow the guide character to be displayed on the display unit to guide a position of the user's eye, wherein the guide character is displayed by being superimposed on the eye image obtained by the camera; and an iris authentication unit for determining whether the image obtained in the eye image pickup apparatus matches a registered iris image,
wherein the display unit of the iris authentication apparatus is employed as the display of the portable telephone,
wherein the guide character includes four arrow characters which are respectively disposed in an upward direction, a downward direction, a left direction and a right direction from a center of an image displayed on the display unit, and
wherein the four arrow characters indicate on the image displayed on the display unit directions in which the user's eye should be moved, said directions including a forward direction, a backward direction and eight radially symmetrical directions that are perpendicular to the forward direction and the backward direction, wherein the eight radially symmetrical directions are the upward direction, the downward direction, the left direction, the right direction, a left upward direction, a right upward direction, a left downward direction and a right downward direction.

15. An eye image pickup method comprising the steps of:
obtaining an eye image by a camera; and
displaying a guide character to guide a position of the eye on a display unit located on a same plane as the position where the lens of the camera is arranged, wherein the guide character is superimposed on the eye image obtained by the camera,
wherein the guide character includes four arrow characters which are respectively disposed in an upward direction, a downward direction, a left direction and a right direction from a center of an image displayed on the display unit, and wherein the four arrow characters indicate on the image displayed on the display unit directions in which the user's eye should be moved, said directions including a forward direction, a backward direction and eight radially symmetrical directions that are perpendicular to the forward direction and the backward direction, wherein the eight radially symmetrical directions are the upward direction, the downward direction, the left direction, the right direction, a left upward direction, a right upward direction, a left downward direction and a right downward direction.

16. The eye image pickup method according to claim 15, wherein the guide character includes a cross-shaped character where an intersection is located at the center of an image displayed on the display unit.

17. The eye image pickup method according to claim 15, wherein the guide character includes a cross-shaped character where an intersection is located at the center of an image displayed on the display unit and a frame-shaped character corresponding to the external circumference of an iris of a predetermined size, and both of the guide characters are displayed at the same time.

18. The eye image pickup method according to claim 15, wherein the guide character includes multiple concentric characters at the center of an image displayed on the display unit.

19. An eye image pickup method comprising the steps of:
obtaining an eye image by a camera; and
displaying a guide character to guide a position of the eye on a display unit located on a same plane as the position where the lens of the camera is arranged, wherein the guide character is superimposed on the eye image obtained by the camera, and wherein the guide character includes multiple concentric characters at the center of an image displayed on the display unit:
turning on or blinking the multiple concentric characters in order from an innermost circle to an outermost circle if an iris in an eye image is smaller than a predetermined size; and
turning on or blinking the multiple concentric characters in order from the outermost circle to the innermost circle if the iris is greater than the predetermined size.

20. The eye image pickup method according to claim 15, further comprising:
displaying at least two of, a cross-shaped character where an intersection is located at the center of an image displayed on the display unit, a frame-shaped character corresponding to the external circumference of an iris of a predetermined size, a directional character indicating a direction in which the eye should be moved, and multiple concentric characters at the center of an image displayed on the display unit.

21. The eye image pickup method according to claim 15, further comprising:
displaying a guide character indicating that a size of an iris image in the eye image has been obtained within a predetermined range.

22. The eye image pickup method according to claim 15, further comprising:
displaying a guide character indicating that a depth of focus of the eye image has been obtained within a predetermined range.

23. The eye image pickup method according to claim 15, further comprising:
changing a color of a background displayed on the display unit, if a size of an iris image in the eye image has been obtained within a first predetermined range and/or a depth of a depth of focus of the eye image has been obtained within a second predetermined range.

24. The eye image pickup method according to claim 15, further comprising:
continuously displaying the eye image as a static image on the display unit if a size of an iris image in the eye image has been obtained within a first predetermined range and/or a depth of a depth of focus of the eye image has been obtained within a second predetermined range.

25. The eye image pickup method according to claim 15, further comprising:
issuing a voice notification if a size of an iris image in the eye image has been obtained within a first predetermined range and/or a depth of a depth of focus of the eye image has been obtained within a second predetermined range.

26. The eye image pickup apparatus according to claim 1, wherein the guide character indicates one of the upward direction, the downward direction, the left direction and the right direction as the direction in which the user's eye should be moved by turning on or blinking the corresponding one of the four arrow characters;
wherein the guide character indicates an intermediate direction between adjacent two arrow characters as the direction in which the user's eye should be moved by turning on or blinking the adjacent two arrow characters;
wherein the guide character indicates the forward direction in which the user's eye approaches the camera by turning on or blinking all of the four arrows so as to direct outward from the center of the image; and
wherein the guide character indicates the backward direction in which the user's eye is farther than the camera by turning on or blinking all of the four arrows so as to direct toward the center of the image.

27. The iris authentication apparatus according to claim 12, wherein the guide character indicates one of the upward direction, the downward direction, the left direction and the right direction as the direction in which the user's eye should be moved by turning on or blinking the corresponding one of the four arrow characters;
wherein the guide character indicates an intermediate direction between adjacent two arrow characters as the direction in which the user's eye should be moved by turning on or blinking the adjacent two arrow characters;
wherein the guide character indicates the forward direction in which the user's eye approaches the camera by turning on or blinking all of the four arrows so as to direct outward from the center of the image; and
wherein the guide character indicates the backward direction in which the user's eye is farther than the camera by turning on or blinking all of the four arrows so as to direct toward the center of the image.

28. The portable terminal according to claim 13, wherein the guide character indicates one of the upward direction, the downward direction, the left direction and the right direction as the direction in which the user's eye should be moved by turning on or blinking the corresponding one of the four arrow characters;
wherein the guide character indicates an intermediate direction between adjacent two arrow characters as the direction in which the user's eye should be moved by turning on or blinking the adjacent two arrow characters;

wherein the guide character indicates the forward direction in which the user's eye approaches the camera by turning on or blinking all of the four arrows so as to direct outward from the center of the image; and wherein the guide character indicates the backward direction in which the user's eye is farther than the camera by turning on or blinking all of the four arrows so as to direct toward the center of the image.

29. The portable telephone according to claim 14, wherein the guide character indicates one of the upward direction, the downward direction, the left direction and the right direction as the direction in which the user's eye should be moved by turning on or blinking the corresponding one of the four arrow characters;

wherein the guide character indicates an intermediate direction between adjacent two arrow characters as the direction in which the user's eye should be moved by turning on or blinking the adjacent two arrow characters;

wherein the guide character indicates the forward direction in which the user's eye approaches the camera by turning on or blinking all of the four arrows so as to direct outward from the center of the image; and wherein the guide character indicates the backward direction in which the user's eye is farther than the camera by turning on or blinking all of the four arrows so as to direct toward the center of the image.

30. The eye image pickup method according to claim 15, wherein the guide character indicates one of the upward direction, the downward direction, the left direction and the right direction as the direction in which the user's eye should be moved by turning on or blinking the corresponding one of the four arrow characters;

wherein the guide character indicates an intermediate direction between adjacent two arrow characters as the direction in which the user's eye should be moved by turning on or blinking the adjacent two arrow characters;

wherein the guide character indicates the forward direction in which the user's eye approaches the camera by turning on or blinking all of the four arrows so as to direct outward from the center of the image; and wherein the guide character indicates the backward direction in which the user's eye is farther than the camera by turning on or blinking all of the four arrows so as to direct toward the center of the image.

* * * * *